United States Patent
Ormachea et al.

(10) Patent No.: US 12,285,293 B2
(45) Date of Patent: Apr. 29, 2025

(54) REVERBERANT SHEAR WAVE GRADIENTS FOR ULTRASOUND ELASTOGRAPHY

(71) Applicant: University of Rochester, Rochester, NY (US)

(72) Inventors: Juvenal Ormachea, Bellevue, WA (US); Kevin J. Parker, Rochester, NY (US)

(73) Assignee: University of Rochester, Rochester, NY (US)

( * ) Notice: Subject to any disclaimer, the term of this patent is extended or adjusted under 35 U.S.C. 154(b) by 189 days.

(21) Appl. No.: 17/657,983

(22) Filed: Apr. 5, 2022

(65) Prior Publication Data

US 2022/0354464 A1    Nov. 10, 2022

Related U.S. Application Data (60) Provisional application No. 63/179,155, filed on Apr. 23, 2021.

(51) Int. Cl.
| | |
|---|---|
| *A61B 8/00* | (2006.01) |
| *G01S 15/89* | (2006.01) |
| *G16H 50/30* | (2018.01) |

(52) U.S. Cl.
CPC ............ *A61B 8/485* (2013.01); *A61B 8/5223* (2013.01); *G01S 15/8977* (2013.01); *G16H 50/30* (2018.01)

(58) Field of Classification Search
CPC ............................ A61B 8/485; G01S 7/52042
See application file for complete search history.

(56) References Cited

U.S. PATENT DOCUMENTS

| | | | | |
|---|---|---|---|---|
| 2007/0038095 A1* | 2/2007 | Greenleaf | ............... | A61B 8/485 600/438 |
| 2008/0249408 A1* | 10/2008 | Palmeri | .................... | A61B 8/08 600/438 |
| 2010/0010346 A1* | 1/2010 | Greenleaf | ............... | A61B 5/442 600/438 |
| 2012/0226158 A1* | 9/2012 | Greenleaf | ............... | A61B 8/485 600/438 |
| 2013/0289402 A1* | 10/2013 | Tabaru | ..................... | A61B 8/08 600/438 |
| 2014/0180091 A1* | 6/2014 | McAleavey | ......... | G01N 29/449 600/438 |

(Continued)

OTHER PUBLICATIONS

K. Parker et al, "Reverberant shear wave fields and estimation of tissue properties", Physics in Medicine and Biology, vol. 6, pp. 1046-1061, 2017 (Year: 2017).*

(Continued)

*Primary Examiner* — Joel Lamprecht
*Assistant Examiner* — Nyrobi Celestine
(74) *Attorney, Agent, or Firm* — Ping Wang; Kaloa Athena Wang PLLC (57) ABSTRACT

The wave number and phase velocity (shear wave speed) of ultrasound energy within an organ of interest are calculated using a herein-disclosed phase gradient calculation method. This calculation method is less sensitive to imperfections in the reverberant field distribution and requires a smaller support window, relative to earlier calculation methods based on autocorrelation. Applications are shown in simulations, phantoms, and in vivo liver.

9 Claims, 9 Drawing Sheets
(9 of 9 Drawing Sheet(s) Filed in Color)

(56) References Cited

U.S. PATENT DOCUMENTS

| | | | | |
|---|---|---|---|---|
| 2014/0350399 | A1* | 11/2014 | Sack | A61B 8/0808 600/438 |
| 2015/0087976 | A1* | 3/2015 | Fan | G01S 7/52042 600/438 |
| 2015/0173718 | A1* | 6/2015 | Tabaru | A61B 8/5207 600/438 |
| 2016/0302769 | A1* | 10/2016 | Labyed | G16H 50/30 |
| 2017/0156701 | A1* | 6/2017 | Urban | A61B 8/5223 |
| 2020/0054217 | A1* | 2/2020 | Parker | A61B 5/7239 |
| 2020/0163649 | A1* | 5/2020 | Urban | A61B 8/485 |
| 2020/0315588 | A1* | 10/2020 | Yasuda | A61B 8/463 |
| 2021/0018606 | A1* | 1/2021 | McCaw | G01N 29/34 |
| 2022/0022846 | A1* | 1/2022 | Correales | A61B 8/485 |

OTHER PUBLICATIONS

A. Tecse et al, "Bidimensional analysis of reverberant shear wave elastography with multiple aleatory mini-surface sources: simulation study", 16th International Symposium on Medical Information Processing and Analysis, pp. 1-9, Nov. 2020 (Year: 2020).*

H. Tzschatzsch et al, "Multifrequency Time-Harmonic Elastography for The Measurement of Liver Viscoelasticity in Large Tissue Windows", Ultrasound in Medicine and Biology, vol. 41, No. 3, pp. 724-733, 2015 (Year: 2015).*

K. Parker et al, "Reverberant shear wave fields and estimation of tissue properties", Physics in Medicine and Biology, vol. 62, pp. 1046-1061, Jan. 2017 (Year: 2017).*

Zvietcovich et al, "Reverberant 3D optical coherence elastography maps the elasticity of individual corneal layers", Nature Communications, vol. 10, No. 4895, p. 1-13, 2019 (Year: 2019).*

J. Ormachea et al, "An initial study of complete 2D shear wave dispersion images using a reverberant shear wave field", Physics in Medicine and Biology, vol. 64, pp. 1-12, Jul. 2019 (Year: 2019).*

G. Flores et al, "Experimental study to evaluate the generation of reverberant shear wave fields (R-SWF) in homogenous media", 2020 IEEE International Ultrasonics Symposium (IUS), pp. 1-4, 2020 (Year: 2020).*

J. Ormachea et al, "Elastography imaging: the 30 year perspective", Physics in Medicine and Biology, vol. 65, Dec. 2020 (Year: 2020).*

J. Ormachea et al, "Shear Wave Speed Estimation Using Reverberant Shear Wave Fields: Implementation and Feasibility Studies", Ultrasound in Medicine and Biology, vol. 44, No. 5, pp. 963-977, Jan. 2018 (Year: 2018).*

Abeysekera J, Rohling R and Salcudean S 2015 Vibro-elastography: Absolute elasticity from motorized 3D ultrasound measurements of harmonic motion vectors. In: 2015 IEEE International Ultrasonics Symposium (IUS), 1-4.

Bracewell R N 1995 Two-dimensional imaging, Chapter 4 (Englewood Cliffs, N.J.: Prentice Hall).

Chen S, Urban M W, Pislaru C, Kinnick R, Zheng Y, Yao A and Greenleaf J F 2009 Shearwave dispersion ultrasound vibrometry (SDUV) for measuring tissue elasticity and viscosity IEEE Trans Ultrason Ferroelectr Freq Control 56 55-62.

Doyley M M 2012 Model-based elastography: a survey of approaches to the inverse elasticity problem Phys Med Biol 57 R35-R73.

Eskandari H, Salcudean S E and Rohling R 2008 Viscoelastic parameter estimation based on spectral analysis IEEE transactions on ultrasonics, ferroelectrics, and frequency control 55 1611-25.

Hetzer S, Hirsch S, Braun J, Sack I and Weygandt M 2019 Viscoelasticity of striatal brain areas reflects variations in body mass index of lean to overweight male adults Brain Imaging Behav.

Hirsch S, Guo J, Reiter R, Papazoglou S, Kroencke T, Braun J and Sack I 2014 MR elastography of the liver and the spleen using a piezoelectric driver, single-shot wave-field acquisition, and multifrequency dual parameter reconstruction Magn Reson Med 71 267-77.

Honarvar M, Lobo J, Mohareri O, Salcudean S E and Rohling R 2015 Direct vibro-elastography FEM inversion in Cartesian and cylindrical coordinate systems without the local homogeneity assumption Phys Med Biol 60 3847-68.

Loupas T, Peterson R B and Gill R W 1995 Experimental evaluation of velocity and power estimation for ultrasound blood flow imaging, by means of a two-dimensional autocorrelation approach IEEE Trans Ultrason Ferroelectr Freq Control 42 689-99.

Muthupillai R, Lomas D J, Rossman P J, Greenleaf J F, Manduca A and Ehman R L 1995 Magnetic-resonance elastography by direct visualization of propagating acoustic strain waves Science 269 1854-7.

Nenadic I, Urban M W, Qiang B, Chen S and Greenleaf J 2013 Model-free quantification of shear wave velocity and attenuation in tissues and its in vivo application J Acoust Soc Am 134 4011-.

Nightingale K R, Rouze N C, Rosenzweig S J, Wang M H, Abdelmalek M F, Guy C D and Palmeri M L 2015 Derivation and analysis of viscoelastic properties in human liver: Impact of frequency on fibrosis and steatosis staging IEEE Trans Ultrason Ferroelectr Freq Control 62 165-75.

Ormachea J, Castaneda B and Parker K J 2018 Shear wave speed estimation using reverberant shear wave fields: implementation and feasibility studies Ultrasound Med Biol doi.org/10.1016/j.ultrasmedbio. 2018.01.011.

Ormachea J and Parker K J 2020a Comprehensive viscoelastic characterization of tissues and the inter-relationship of shear wave (group and phase) velocity, attenuation and dispersion Ultrasound Med Biol 46 3448-59.

Ormachea J and Parker K J 2020b Elastography imaging: the 30 year perspective Phys Med Biol.

Ormachea J, Parker K J and Barr R G 2019 An initial study of complete 2D shear wave dispersion images using a reverberant shear wave field Phys Med Biol.

Papoulis A 1987 The Fourier integral and its applications, Chapter 4.4 (New York: McGraw-Hill).

Parker K J and Maye B A 1984 Partially coherent radiation from reverberant chambers J Acoust Soc Am 76 309-13.

Parker K J, Ormachea J, Zvietcovich F and Castaneda B 2017 Reverberant shear wave fields and estimation of tissue properties Phys Med Biol 62 1046-61.

Plewes D B, Betty I, Urchuk S N and Soutar I 1995 Visualizing tissue compliance with MR imaging J Magn Reson Imaging 5 733-8.

Sinkus R, Lorenzen J, Schrader D, Lorenzen M, Dargatz M and Holz D 2000 High-resolution tensor MR elastography for breast tumour detection Phys Med Biol 45 1649-64.

Turgay E, Salcudean S and Rohling R 2006 Identifying the mechanical properties of tissue by ultrasound strain imaging ultrasound Med Biol 32 221-35.

Tzschatzsch H, Nguyen Trong M, Scheuermann T, Ipek-Ugay S, Fischer T, Schultz M, Braun J and Sack I 2016 Two-dimensional time-harmonic elastography of the human liver and spleen Ultrasound Med Biol 42 2562-71.

Weaver J B, Van Houten E E, Miga M I, Kennedy F E and Paulsen K D 2001 Magnetic resonance elastography using 3D gradient echo measurements of steady-state motion Med Phys 28 1620-8.

Wu Z, Taylor L S, Rubens D J and Parker K J 2004 Sonoelastographic imaging of interference patterns for estimation of the shear velocity of homogeneous biomaterials Phys Med Biol 49 911-22.

Zvietcovich F, Pongchalee P, Meemon P, Rolland J P and Parker K J 2019 Reverberant 3D optical coherence elastography maps the elasticity of individual corneal layers Nat Commun 10 4895-1--13.

* cited by examiner

REVERBERANT SHEAR WAVE GRADIENTS FOR ULTRASOUND ELASTOGRAPHY

SUMMARY OF THE INVENTION

The invention relates to diagnostic medical imaging, and more particularly relates to elastography. In its most immediate sense, the invention relates to ultrasound elastography, as well as to magnetic resonance elastography and to optical coherence elastography.

Some soft tissue diseases (including but not limited to some cancers) cause the diseased region to have viscoelastic properties that are different from those of the surrounding non-diseased tissue. For example, a breast tumor may be stiffer than the surrounding healthy breast tissue.

Ultrasonic elastography can be used in vivo to localize diseased regions within an organ. In an ultrasonic elastography study, shear-inducing transducers acting as vibration sources introduce acoustic energy into the organ of interest, generating shear waves within the organ and causing the organ tissue to distort. By localizing the regions where the distortion changes and measuring the distortion (and thereby determining the stiffness or dispersion) of those regions, the locations and severities of the disease can be determined.

One type of ultrasound elastography utilizes a reverberant field (also known as a reverberant shear wave field). In this technique, one or more shear-inducing transducers are used to create a profusion of shear waves along many different directions. This diversity of differently-directed shear waves is also enhanced by all the reflections that naturally occur from the boundaries of the organ and from the inhomogeneities within it.

It is possible to estimate shear wave speed ("SWS") and soft tissue stiffness and then the soft tissue dispersion which is the SWS change with frequency and is related to the lossy and attenuating nature of tissue. However, in the past such estimations required the use of autocorrelation with a wide autocorrelation window. This could limit the spatial resolution of the shear wave speed map that indicates the position of a suspect structure in the organ under examination. Also, there are conditions where the shear wave field may not be uniformly reverberant. Such conditions are created in locations close to a strong vibration source producing vibrations only in one direction.

The invention proceeds from the realization that when two characteristics of a reverberant field—namely, the wavenumber and the phase velocity (shear wave speed)—are calculated in a new and unique way using the herein-disclosed phase gradient ("PG") calculation method, they produce new and unexpectedly advantageous results. More specifically, these uniquely-calculated quantities permit a tumor (or other stiff or dispersive region within an organ under examination) to be accurately localized even if it is in a location where the reverberant shear wave field is not homogeneous (because e.g. the tumor is close to a strong vibration source). It is unnecessary to use autocorrelation. Additionally, because the herein-disclosed PG calculation method requires a smaller region of support than does prior art autocorrelation, the PG method holds out the promise of improved spatial resolution and reduced need for computational resources.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will be better understood with reference to the exemplary and non-limiting drawings, in which:

FIG. 3 illustrates the results of a simulation carried out in "pre-reverberant" and reverberant shear wave fields showing an inclusion in a homogeneous medium. (a) Representation of the inclusion and homogeneous media. The shear wave speed for the inclusion and the background are 3.0 and 2.0 m/s, respectively. (b) Illustration of different regions (shear wave phase zones or "SWP" zones) where shear waves behave as a dominant unidirectional wave (zones 1, 2, and 3) and as a reverberant shear wave field (zone 4). (c) Phase map of the propagating shear waves, showing that for regions 1, 2, and 3, planes waves are propagating at different directions. For region 4, a clear reverberation field is observed. The red dashed circle illustrated the inclusion location. (d) Final shear wave speed image applying the here-disclosed phase gradient calculation method. The black dashed circle illustrates the location of the inclusion.

FIG. 5 shows elastography images corresponding to the CIRS breast phantom showing a stiffer inclusion, its B-mode image, and the dispersion curve. The SWS image obtained with acoustic radiation force ("ARF") using a Samsung Model RS85 system is shown on the top left corner. The SWS images obtained with the phase gradient method are shown on the top and bottom rows corresponding to different vibration frequencies: 200 Hz, 400 Hz, 600 Hz, 900 Hz, and 1 kHz. The bottom right corner shows the dispersion curve including phase velocity values (mean±standard deviation (SD)) for the Samsung data and the results obtained in this study. The mean and SD were extracted for a ROI at each image. The ROI position is illustrated as a red dashed rectangle in the B-mode image. For this case, phase velocity values almost remain the same for different frequencies, indicating that the material is almost purely elastic. The dispersion curve represents a direct comparison between the Samsung system and the PG method. In addition, the blue dashed lines denote a linear fitting, and the red dashed lines denote a power law fitting. The orange shaded region represents the −6 dB frequency range criteria for the ARF-based signals. More detail about this criterion can be found in Ormachea J and Parker K J, 2020 *Comprehensive viscoelastic characterization of tissues and the inter-relationship of shear wave (group and phase) velocity, attenuation and dispersion Ultrasound Med Biol* 46 3448-59.

FIG. 6 shows elastography images corresponding to the CIRS viscoelastic phantom, its B-mode image, and the dispersion curve. The SWS image obtained with ARF using the Samsung system is shown on the top left corner. The SWS images obtained with the PG method are shown on the top and bottom rows corresponding to different vibration frequencies: 100 Hz, 150 Hz, and 200 Hz. The bottom right corner shows the dispersion curve including phase velocity values (mean±SD) for the Samsung data and the results obtained in this study. The mean and SD were extracted for a ROI at each image. The ROI position is illustrated as a red dashed rectangle in the B-mode image. For this case, phase velocity values increase as a function of frequency, indicating that the material has viscoelastic properties. The dispersion curve represents a direct comparison between the Samsung system and the here-disclosed PG method. In addition, the blue dashed lines denote a linear fitting, and the red dashed lines denote a power law fitting. The orange shaded region represents the −6 dB frequency range criteria for the ARF-based signals.

FIG. 7 shows elastography images corresponding to in vivo liver tissue. The SWS images obtained with the phase gradient method are shown in the top rows, corresponding to two vibration frequencies: 100 and 300 Hz. Each of them has its corresponding B-mode image and a snapshot of the reverberant shear wave field to the left. Some regions do not show SWS information because the corresponding particle displacement was neglected due to its low SNR, as explained in section 2. D. below. The bottom left corner shows two particle displacement examples located at specific lateral and axial positions (x, z) with their corresponding spectrum to illustrate that the maximum peak corresponds to the applied vibration frequency. The bottom right corner shows the dispersion curve including phase velocity values (mean±SD) for the results obtained in this study. The mean and SD were extracted for a ROI at each image. The ROI's position is illustrated as a red dashed rectangle in the B-mode image. For this case, phase velocity values increase as a function of frequency, indicating that liver tissue has viscoelastic properties. In addition, the blue dashed line denotes a linear fitting, and the red dashed line denotes a power law fitting. The orange shaded region represents the frequency range used to estimate the linear and power law fittings.

FIG. 8 is a comparison of SWS images created using the autocorrelation method (a and b) and the herein-disclosed phase gradient method (c) in the CIRS breast phantom at 900 Hz. Both methods require a local window to estimate the wavenumber k (window size is shown above each SWS image). Case (a) is not able to reconstruct the elastography image properly and reports overestimated values of SWS since it does not have enough points, due the small window size, to approximate the theoretical curve. On the other hand, case (b) shows a better result, based on the autocorrelation method, when the window size is increased. Case (c) uses same window size as case (a) and shows an improvement for the SWS. This indicates that the phase estimator is less sensitive to imperfections in the reverberant field distribution and requires a smaller support window than case (b).

DETAILED DESCRIPTION OF PREFERRED EMBODIMENTS

1. The Basis of the Herein-Disclosed Phase Gradient ("PG") Method

Figure 1:
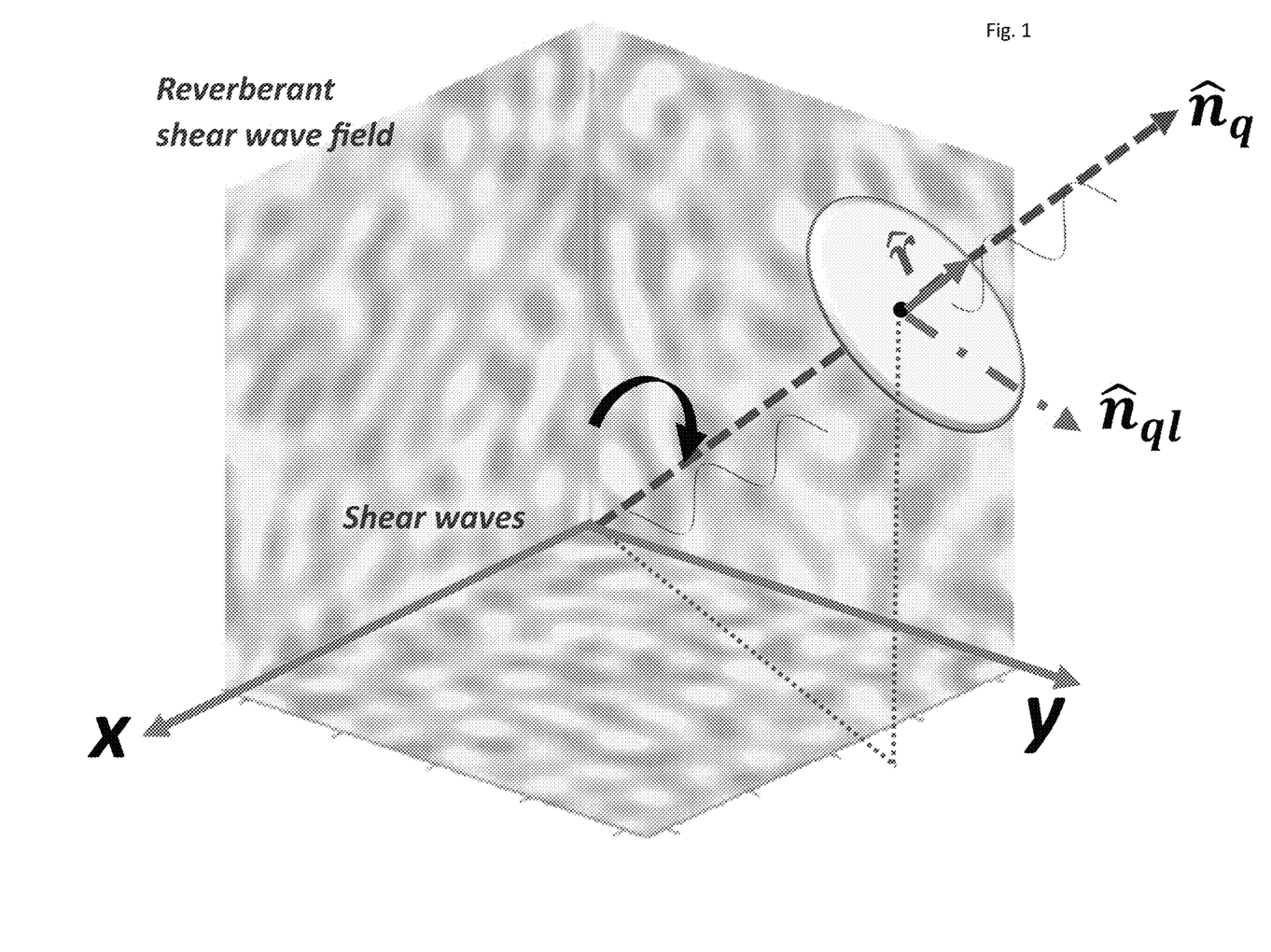
FIG. 1 is a schematic illustration of the orientation of a shear-inducing transducer (left, which could be ultrasound, magnetic resonance, or optical coherence tomography), and the body under investigation, which has an isotropic random distribution of shear waves propagating through the interior, consistent with the theory of reverberant fields. The x-axis of the coordinate system is aligned with the axial direction of the imaging transducer, and the imaging system is assumed to detect motion in the x-direction. The $n_q$ are the propagation direction vectors of the q individual plane waves that are distributed throughout the reverberant interior.

In a fully developed reverberant field the complex pressure and velocity fields at a position ε within the interior can represented as the superposition of plane waves incident from all directions. In that case, the vector velocity V can be written as a function of position ε:

$$v(t, \varepsilon) = \sum_{q,l} n_{ql} v_{ql} e^{i(k_0 n_q \cdot \varepsilon - \omega_0 t)} \quad (1)$$

and where the x component of the velocity is:

$$v_x(t, \varepsilon) = \hat{e}_x \cdot v(t, \varepsilon) = \sum_{q,l} n_{ql_x} v_{ql} e^{i(k_0 n_q \cdot \varepsilon - \omega_0 t)} \quad (2)$$

$$n_{ql_x} = n_{ql} \cdot \hat{e}_x \quad (3)$$

where the index q represents direction, $n_q$ are unit vectors uniformly distributed around $4\pi$ solid angle, $k_0$ and $\omega_0$ are the wavenumber and radial frequency of the plane waves, respectively, and $\hat{v}_q$ are independent, identically distributed variable of varying magnitude and phase. Taking a snapshot at some fixed reference time $t_0$, and recognizing that $n_{xq}\hat{v}_q$ are independent of position, we write an ersatz representation of the field as:

$$v_x(\varepsilon) = V_0 e^{i\phi(\varepsilon)} \quad (4)$$

where $V_0$ is related to the root mean square amplitude of the field and $\phi(\varepsilon)$ is the spatially varying phase. From Parseval's theorem and the derivative properties of Fourier transforms, following Papoulis A 1987 *The Fourier integral and its applications*, Chapter 4.4 (New York: McGraw-Hill) we may equate the second moment of the power spectrum to the derivative of phase. These steps are as follows. Let P(k) be the one-dimensional spatial Fourier transform of $v_x(\varepsilon)$ and where k is the spatial frequency. The power spectrum $|P(k)|^2$ of this function is already known from the ensemble-averaged autocorrelation function $\langle v_x(\varepsilon) v_x(\varepsilon + \Delta\varepsilon) \rangle$ derived previously and can be expressed in terms of spherical Bessel functions. This function depends on the angle $\theta$ between the imaging system's axis (the direction of detection of motion, the x-axis in FIG. 1) and the direction of $\Delta\varepsilon$ chosen for the autocorrelation function. For an isotropic medium the autocorrelation function $B_{iso}$ is:

$$B_{iso}(\Delta\varepsilon, \Delta t) = \overline{V_0^2} e^{i\omega_0 \Delta t} \left\{ \frac{\sin^2\theta_s}{2} \left[ j_0(k_0 \Delta\varepsilon) - \frac{j_1(k_0 \Delta\varepsilon)}{k_0 \Delta\varepsilon} \right] + \cos^2\theta_s \frac{j_1(k_0 \Delta\varepsilon)}{k_0 \Delta\varepsilon} \right\}, \quad (5)$$

where $j_1$ represents the spherical Bessel functions of order 1, and $\theta_s$ is the angle between $\Delta\varepsilon$ and $\hat{e}_x$.

Next we examine the derivative of one realization of the field and the corresponding Fourier transform of that function. Denoting:

$$\Im\{v_x(\varepsilon)\} = V_0 P(k) \quad (6)$$

$$\Im\left\{\frac{d}{d\varepsilon}v_x(\varepsilon)\right\} = jkV_0 P(k) \quad (7)$$

Now, by taking the magnitude square and equating the two domains using Parseval's theorem, we have, with substitution from eqn (4):

$$\int \left|\frac{d}{d\varepsilon}v_x(\varepsilon)\right|^2 d\varepsilon = \frac{V_0^2}{2\pi} \int |(jk)P(k)|^2 dk \quad (8)$$

$$\int \left|jV_0\left(\frac{d}{d\varepsilon}\phi(\varepsilon)\right)e^{j\phi(\varepsilon)}\right|^2 d\varepsilon = \frac{V_0^2}{2\pi}\int k^2|P(k)|^2 dk$$

$$\int \left|\frac{d}{d\varepsilon}\phi(\varepsilon)\right|^2 d\varepsilon = \frac{1}{2\pi}\int k^2|P(k)|^2 dk.$$

The right side is also recognized as the second moment $m_s^2$ of the power spectrum of the RSW field, which has been derived previously and is strictly bandlimited to $\pm k_0$. Specifically for the transverse case ($\theta = \pi/2$):

$$|P(k)|^2 = \frac{\sqrt{\frac{\pi}{2}}(k_0^2 + k^2)}{4k_0^3} \text{ for } |k| \leq k_0. \quad (9)$$

To determine the second moment, using s for the spatial frequency variable of integration and considering the orthogonal direction to the measurement axis, we find:

$$m_s^2 = \int_{-k_0}^{k_0}(s^2)\frac{\sqrt{\frac{\pi}{2}}(k_0^2 + s^2)}{4k_0^3}ds = \frac{\sqrt{8\pi}}{15}k_0^2 \quad (10)$$

for transverse direction of the displacement with respect to the imaging system's axis. Then, interpreting the left-hand side of eqn (8) as an ensemble average:

$$k_0^2 = C\left\langle\left|\frac{d\phi}{d\varepsilon}\right|^2\right\rangle, \quad (11)$$

where the brackets indicate the average value over some homogeneous region and where C is a scale constant that can be also determined experimentally using a known reference material.

This analysis can also be extended to two-dimensional estimates. It can be shown that the key relationships including Parseval's theorem (and the related Rayleigh integral theorem), the derivative theorem, and the second moment theorem all have direct extensions to two dimensional Fourier transforms Bracewell R N 1995 *Two-dimensional imaging, Chapter* 4 (Englewood Cliffs, N.J.: Prentice Hall). Thus, using phase unwrapping we estimate the phase information across a reverberant field in two transverse dimensions approximately as $$\phi(x,z) \cong k_x x + k_z z + c_0 \quad (12)$$

and the wavenumber estimation is formed from $$k^2 \approx C\left\langle\left|\frac{d\phi}{d\varepsilon}\right|^2\right\rangle = C(k_x^2 + k_z^2). \quad (13)$$

Finally, the phase velocity or SWS can be determined by $$c_s = \frac{2\pi f}{k}, \quad (14)$$

where f is the corresponding vibration frequency. In the case where the two axes of an image plane are oriented as transverse and axial with respect to the detection of velocity, then the $k_x$ and $k_z$ will require different scale factors, since the autocorrelation function depends on orientation as given in eqn (5).

As has been shown above, the herein-disclosed phase gradient ("PG") calculation method yields an estimate of wavenumber and phase velocity (shear wave speed) without the use of autocorrelation.

2. Experimental Validation of Wavenumber and Phase Velocity Using the Phase Gradient Method a. Ultrasound System and Data Acquisition A Verasonics system (Vantage-128™, Verasonics, Kirkland, WA, USA) connected to a convex ultrasound probe (model C4-2, ATL, Bothell, WA, USA) or a linear ultrasound probe (model L7-4, ATL, Bothell, WA, USA) was applied. This system was used to track the induced displacements using a Loupas estimator (Loupas et al., 1995). The linear probe was used for the breast phantom, whereas the convex probe was used for scanning deeper into the viscoelastic phantom and liver tissue. The center frequencies were 2.98 MHz and 5.21 MHz for the convex and linear probes, respectively. The sampling frequency were 12 MHz and 20 MHz for the convex and linear probes, respectively. The tracking pulse repetition frequency (PRF) was set to 3600 Hz and 5000 Hz for the convex and linear probes, respectively. The total acquisition time was 0.25 seconds.

b. Vibration Sources and Vibration Frequency Range

A custom-made portable trifold futon (70×60×10 cm³) with multiple embedded vibration sources (Quad Resonator Model EI718™, Elastance Imaging LLC, Columbus, OH, USA) was mounted to a clinical bed to generate the reverberant shear wave field. The precise details of the active source configuration are proprietary to Elastance Imaging LLC. Vibration frequency ranges between 100-1000 Hz were used for the breast CIRS phantom, whereas 100-400 Hz for the viscoelastic and in vivo liver experiments.

c. Scans of Phantoms and the Human Liver In Vivo

Two calibrated phantoms were used in this study. The first was a CIRS breast phantom (Model 059, Computerized Imaging Reference Systems, Norfolk, VA, USA) with background (20 kPa nominal Young's modulus) and inclusion regions (at least two times stiffer than the background region per the manufacturer's datasheet). The other phantom was a custom made CIRS (Serial No. 2095.1-1, Computerized Imaging Reference Systems) homogeneous viscoelastic phantom (6 kPa nominal Young's modulus). Additionally, one liver tissue from a volunteer was scanned on the custom bed. The scan was conducted under the requirements of informed consent of the University of Rochester Research Subjects Review Board.

d. Computation of Wavenumber and Phase Velocity

Figure 2:
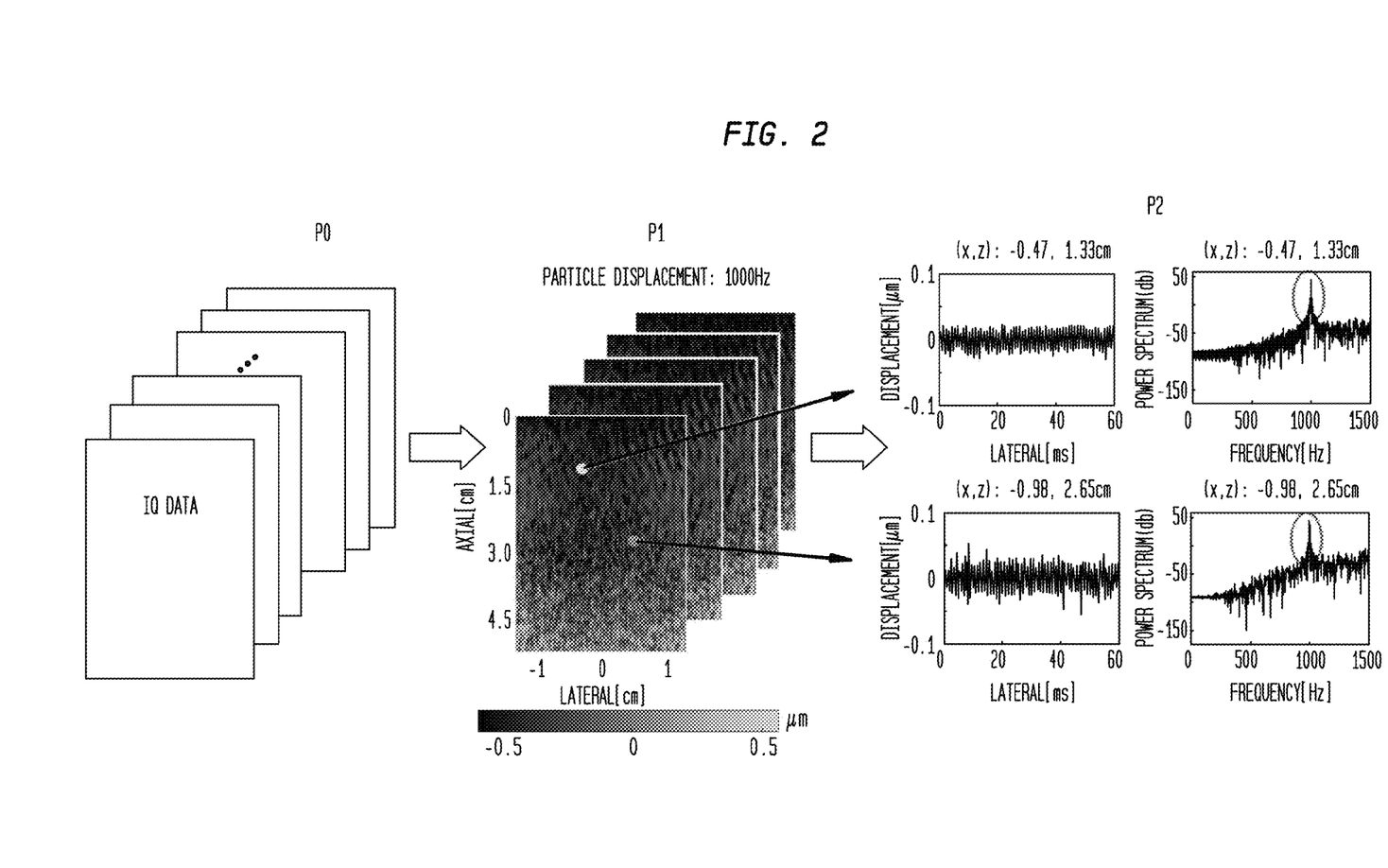
FIG. 2 schematically illustrates the six step process used to obtain the two-dimensional shear wave speed maps for their corresponding vibration frequency. Arrows connect the illustrations to show the process flow from the initial step P0 to the final step P5.

FIG. 2 summarizes the process to obtain the 2D SWS maps for their corresponding vibration frequency using the phase-gradient method in a reverberant shear wave elastography (R-SWE) field. 'P0' estimates the particle displacements, in the axial direction, using a Loupas estimator. 'P1' shows some snapshots of a typical R-SWE field using a 1 kHz vibration frequency. Then, 'P2' illustrates the particle velocity in time and its corresponding frequency spectrum showing the maximum peak at 1 kHz. Then, the signal to noise ratio (SNR) of the particle velocity signals were measured; the regions with SNR<10 dB were neglected and were not used for later steps. After taking the magnitude and phase at the peak, 'P3' applies an additional 2D bandpass spatial filter to remove compressional waves and reduce noise in all directions as in Ormachea et al. (2018; 2019b). 'P4' applies the phase-gradient method to obtain the correspondent wavenumber by taking a small region of interest (1.34×1.34 mm² at 1 kHz, with 1 pixel/0.14 mm) of the unwrapped phase values. The unwrapped phase is fitted to eqn (12) using the MATLAB curve-fitting toolkit (The MathWorks, Natick, MA, USA) based on a robust linear least square minimization method. From eqn (12) the wavenumber is calculated using eqn (13). The 2D wavenumber map is obtained by repeating 'P4' at different pixel locations. Then, the SWS is obtained using eqn (14). Finally, 'P5' smooths the 'raw' SWS map by applying an averaging filter and eliminates the edges.

d. Comparison with Shear Wave Elastography Based on Acoustic Radiation Force (ARF)

A Samsung ultrasound system (Model RS85, Samsung Medison Co. Ltd., Seoul, South Korea) was used in order to obtain elastography images for comparison purposes. Displacement waveforms were tracked over time and the phase velocity was obtained by calculating the 2D Fourier transform from the particle velocity signals and finding the maximum amplitude at spatial frequency $k(\omega)$ for each discrete temporal frequency. The specific data acquisition and post-processing details to obtain the phase velocity information are described by Ormachea J and Parker K J, 2020 *Comprehensive viscoelastic characterization of tissues and the inter-relationship of shear wave (group and phase) velocity, attenuation and dispersion Ultrasound Med Biol* 46 3448-59.

e. Monte Carlo Simulation

Figure 3:
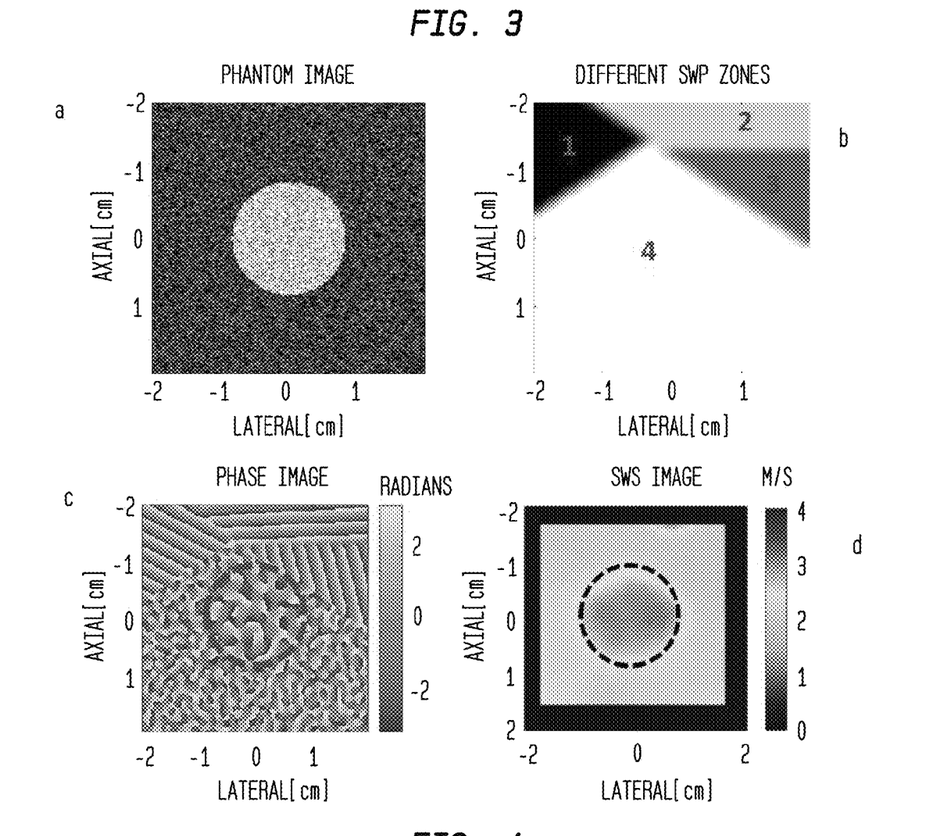

A 40×40×40 mm³ field (0.3 mm sampling resolution) was generated in MATLAB (The MathWorks, Inc. Natick, MA, USA) to simulate a reverberant shear wave field in an linear-elastic medium to validate the SWS estimator. The medium, illustrated in FIG. 3(a), shows the field containing a harder inclusion ($c_s$=3.0 m/s) surrounded by a softer background ($c_s$=2.0 m/s). The reverberant field was created with a total of 1000 realizations of random variables: $\hat{n}_q$ is defined by the angles of the basis vectors φ and θ (see FIG. 1), both covering a range of [0, 2π] radians; the scalar $v_q$ covers a range of [−1, 1] m/s representing the particle velocity amplitude. The random realizations generate a spatial and complex valued particle velocity field $V(\varepsilon)=V(\varepsilon)e^{-j\omega t}$, where $\omega_0=2\pi f_0$ with f=900 Hz and $k=c_s/\omega_0$. In addition, a hybrid regional model was made of imperfect reverberant fields comprised of three dominant shear waves propagating at different directions through the entire field. Then, four different binary masks with smooth edges were created. Each of them was designed with a particular shape, as can be observed in FIG. 3(b), and applied. Regions 1, 2, and 3 were designated for each of the individual plane shear waves simulations and region 4 was selected for the reverberant simulation. After multiplication of each simulation with its corresponding mask, all the results were superimposed to replicate a region of interest containing three unidirectional shear waves and one reverberant field. This simulates the presence of various dominant unidirectional shear waves propagating in some regions (areas 1, 2, and 3 in FIG. 3(b)) of the field, where there is not a sufficient number of waves over all directions to produce a reverberant shear wave field or in proximity to a strong external source. Thus, the simulation also evaluates if the phase gradient method could measure the corresponding shear wave speed in less ideal or "pre-reverberant" condition.

3. Experimental Validation Results

FIG. 3 shows the simulated media illustrating a "pre-reverberant" and reverberant shear wave fields. FIG. 3(c) shows the shear wave phase map and shows the unidirectional propagation in regions 1, 2, and 3 (FIG. 3(b)) and the reverberant shear wave field in region 4 (FIG. 3(b)). FIG. 3(d) shows the final SWS image applying the phase gradient method. The mean and standard deviations for the inclusion and background at 900 Hz are 2.96±0.08 m/s, and 2.10±0.07 m/s, respectively, showing good agreement with the SWS values used for the simulation for the inclusion m/s ($c_s$=3.0), and the background ($c_s$=2.0 m/s).

Figure 4:
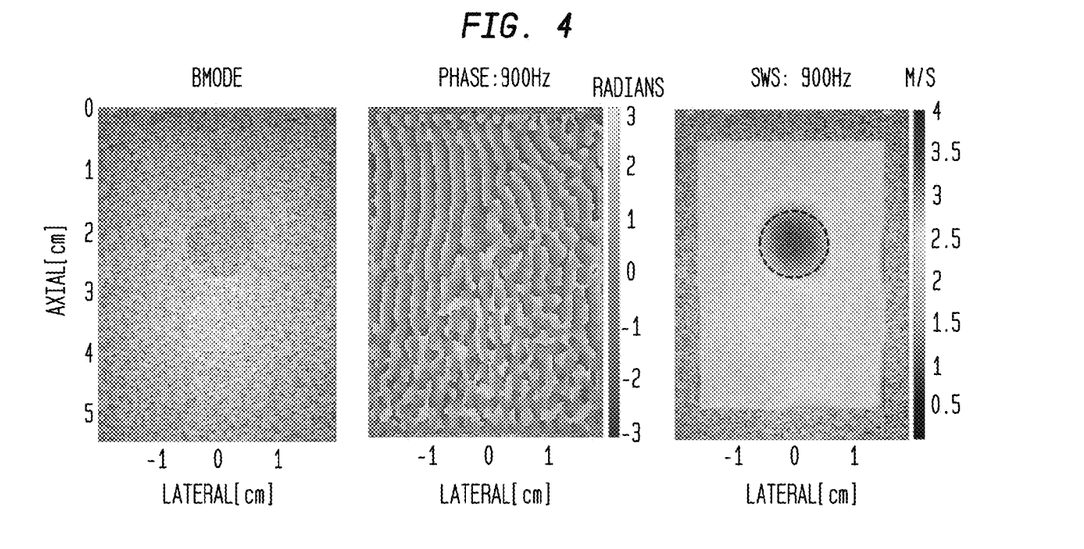
FIG. 4 illustrates shear waves propagating at different directions creating a reverberant field and dominant unidirectional waves in a "pre reverberant" field (e.g. top left corner). As illustrated in the simulations, the here-disclosed phase gradient calculation method is able to estimate the shear wave speed for both conditions. At the left is a B-mode image of a breast phantom manufactured by Computerized Imaging Reference Systems, Inc. ("CIRS") showing the harder inclusion. In the center is the phase map of the propagating shear wave at 900 Hz. At the right is the final SWS image showing the harder inclusion and the background. The black dashed circle illustrates the location of the inclusion.

FIG. 4 shows (from left to right) the B-mode, shear wave phase map, and the SWS image for the CIRS breast phantom vibrating at 900 Hz. As illustrated in the simulated case in FIG. 3, a "pre-reverberant" zone and more ideal reverberant shear wave regions can be observed within the entire region of interest. The final SWS image using the phase gradient method shows good performance in estimating a consistent SWS for both shear wave fields. The mean SWS and the standard deviations for the inclusion and the background are 3.43±0.24 m/s, and 2.27±0.19 m/s, respectively. The CIRS data sheet for this phantom indicates that the background is 20 kPa (~2.58 m/s) Young's modulus and at least 2× harder (40 kPa, ~3.65 m/s) for the inclusions.

Figure 5:
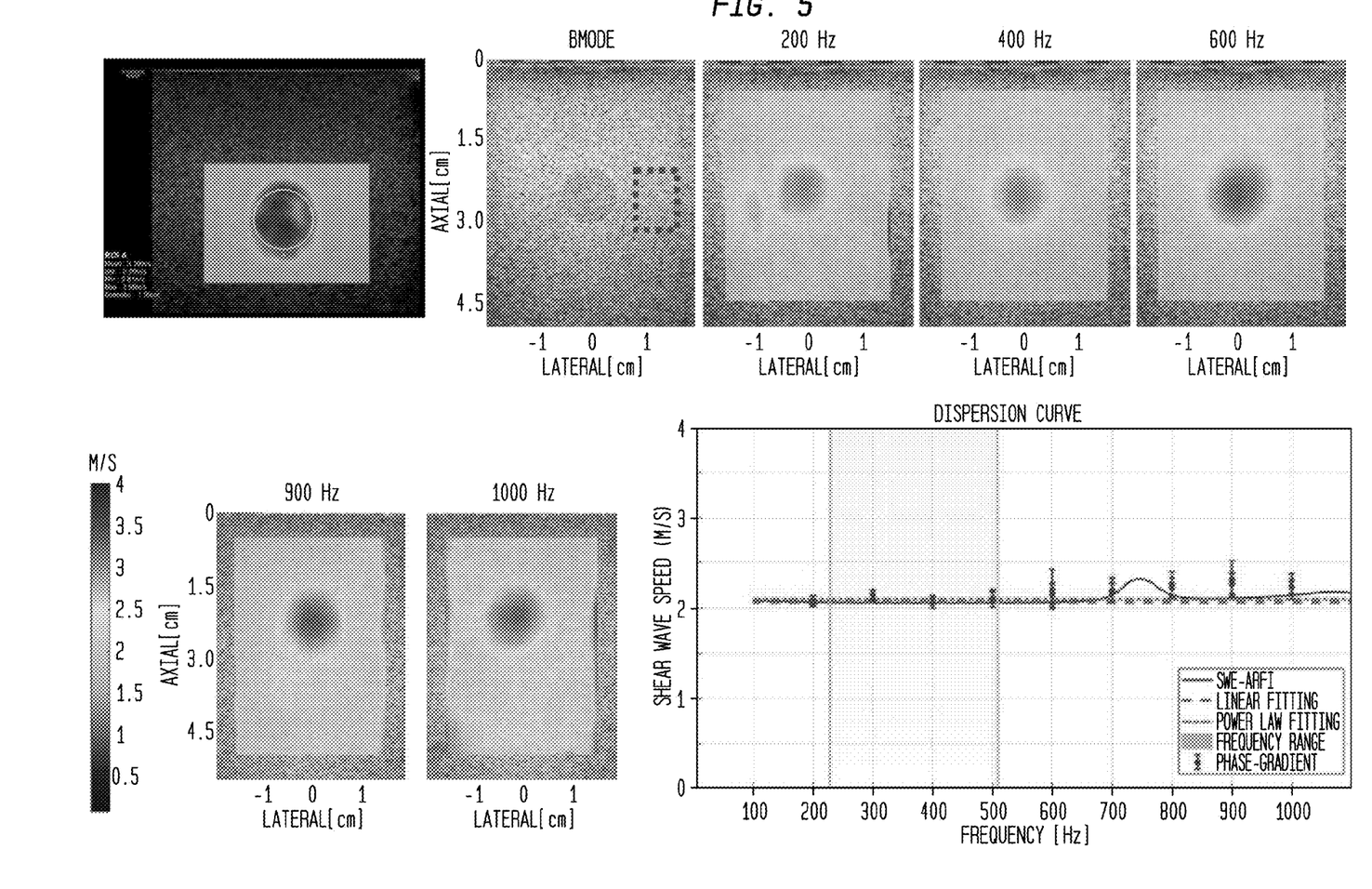

FIG. 5 shows a comparison of SWS results for the CIRS breast phantom using a commercial system (Samsung RS85, Samsung Medison Co. Ltd., South Korea) and the phase gradient method for different vibration frequencies. Since the commercial elastography image is based on ARF, the measured SWS is a group velocity value, whereas the phase gradient method measures the phase velocity. For that reason, the dispersion curve, for a background region, was obtained for both methods to perform a direct comparison in terms of phase velocity. As observed, a good agreement between both methods was obtained. For example, the phase velocity at 600 Hz, is 2.14±0.09 and 2.2±0.13 for the Samsung system and the phase gradient method, respectively. In this case the dispersion curve remains almost constant since the phantom is an almost purely elastic phantom.

Figure 6:
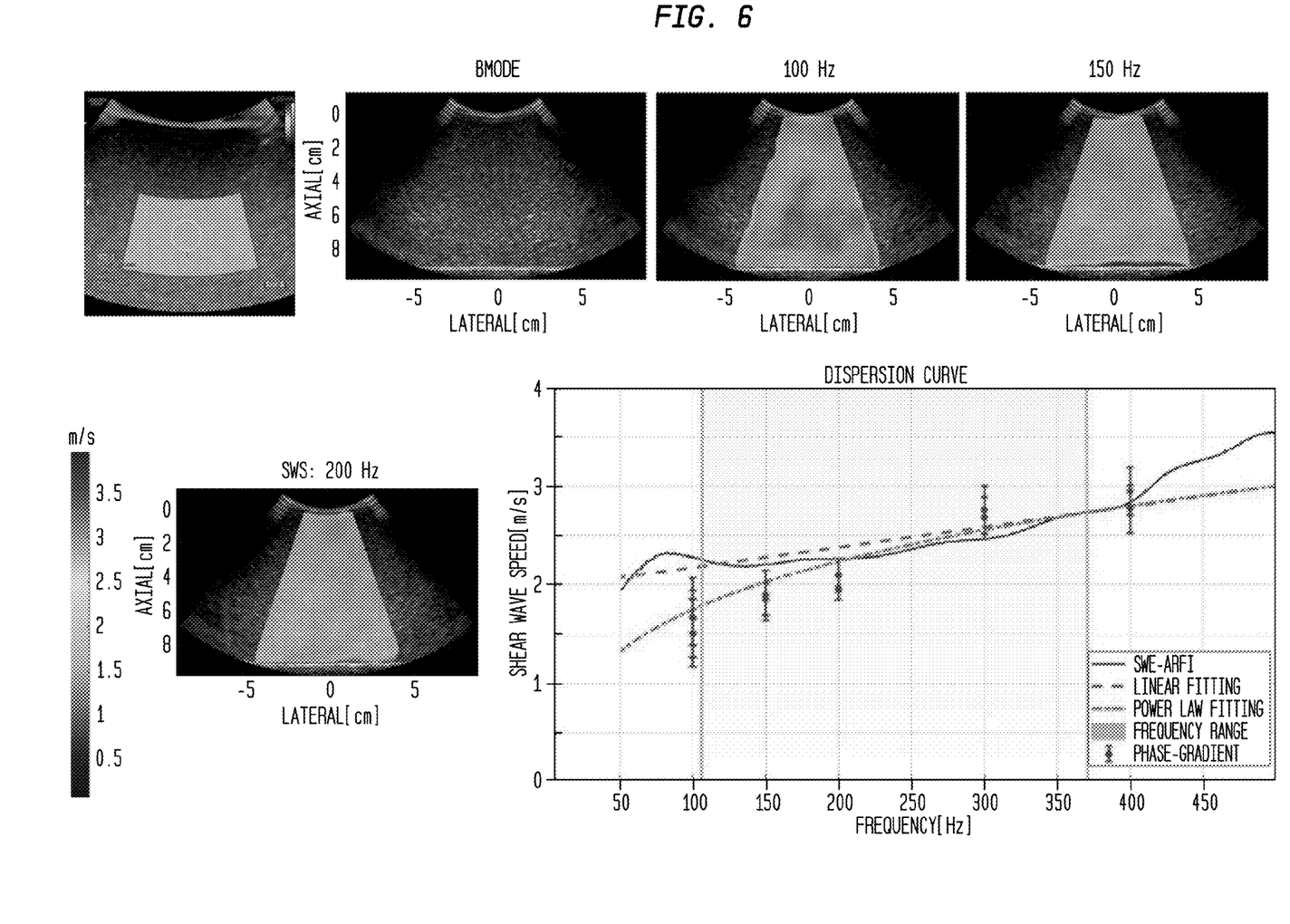

FIG. 6 shows a comparison of SWS results for the custom-made CIRS viscoelastic phantom using a commercial system (Samsung RS85) and the phase gradient method for different vibration frequencies. Similar to the CIRS breast phantom case, the dispersion curve was obtained for both methods to perform a direct comparison in terms of phase velocity. As shown, a good agreement between both methods was obtained. For example, the phase velocity at 150 Hz, is 2.21±0.18 and 1.90±0.25 for the Samsung system and the phase gradient method, respectively. It can also be noticed that the phase velocity increases as a function of frequency since the phantom is a viscoelastic material.

Figure 7:
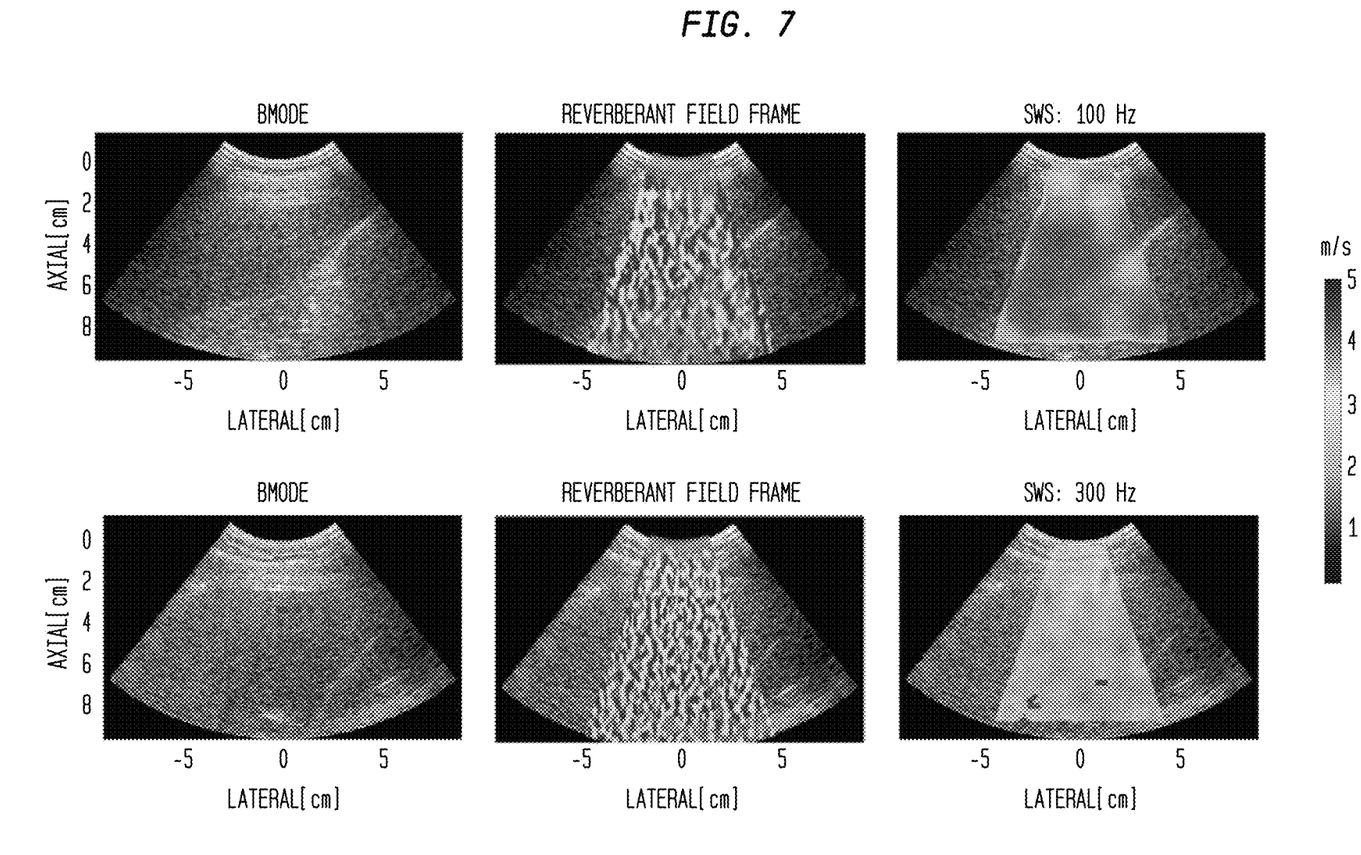

FIG. 7 shows SWS images for an in vivo liver tissue result applying different vibration frequencies. A distinction between fat/muscle and liver tissue were obtained for frequencies higher than 150 Hz. Reverberant shear wave fields were obtained for the total field of view and complete SWS images were obtained for the liver that is located between 3.5-9 cm depth.

Figure 8:
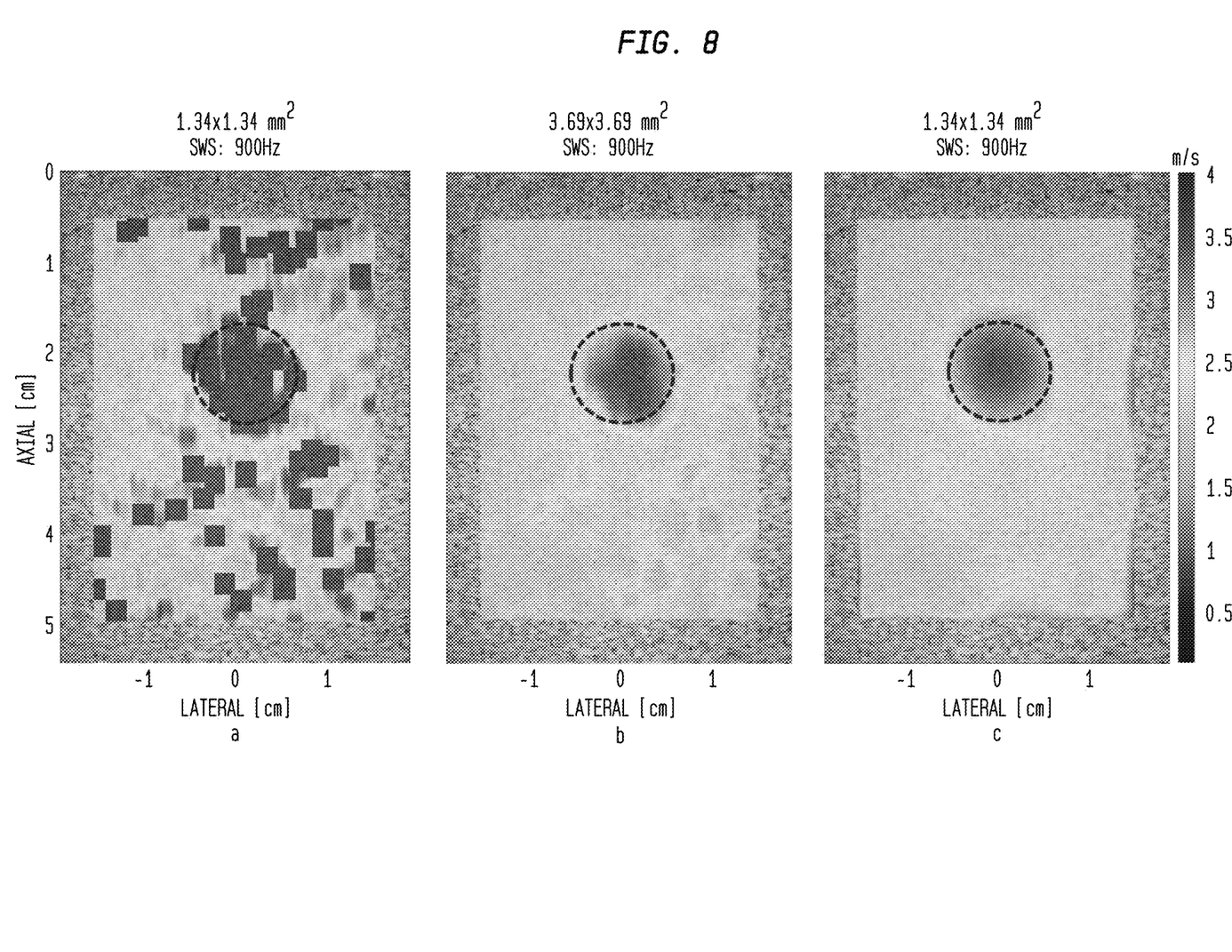

As can be seen in FIG. 8, the phase gradient calculation method is able to measure the SWS using smaller support regions than the autocorrelation calculation method. This is important because a smaller window may improve the spatial resolution and require less computational resources to process the entire field of view. FIG. 8 also shows that another advantage of the phase gradient calculation method is that it appears robust under a variety of wave types. For example, in "pre-reverberant" fields where there is an insufficient number of waves over all directions to produce a close match to eqn (5), the rate of change of phase still approaches a stable estimate related to k and sensitive to local contrast, as demonstrated in the simulation and phantom experiments represented in FIG. 3 and FIG. 4. Moreover, FIG. 8 shows that the autocorrelation method estimates have more variation with respect to the orientation of the dominant field direction.

Although a preferred embodiment has been described above, the scope of the invention is defined only by the claims, which follow:

The invention claimed is:

1. A method of determining a viscoelastic property of a body region of a living subject at a plurality of points within the body region, comprising the following steps:
   a. establishing a reverberant field within the body region, wherein the reverberant field comprises multiple differently-directed shear waves and all reflections that naturally occur from the body region's boundaries and any inhomogeneities within the body region;
   b. measuring a phase at each said plurality of points of the reverberant field;
   c. computing, at each said plurality of points of the reverberant field, a positional rate of change of each said phase with respect to positional change within the body region to determine a wavenumber, wherein the wavenumber is estimated by directly relating a spatial derivative of phase to the wavenumber as defined over a multi-dimensional wave field using the proportionality of the spatial derivative in multiple dimensions of phase to the wavenumber; and
   d. determining, from said wavenumber and corresponding frequency, a viscoelastic property of the body region at each said plurality of points of the reverberant field.

2. The method of claim 1, wherein the establishing step comprises using at least one vibration source to create a reverberant field of shear waves within the body region.

3. The method of claim 2, the establishing step comprises subjecting the body region to vibration delivered at a plurality of frequencies.

4. The method of claim 1, wherein the body region is the liver.

5. The method of claim 1, wherein the viscoelastic property is stiffness.

6. The method of claim 1, wherein the viscoelastic property is dispersion.

7. The method of claim 2, wherein said at least one vibration source is a shear-inducing.

8. The method of claim 3, wherein the establishing step comprises subjecting the body region to shear-inducing vibration delivered at a plurality of frequencies.

9. The method of claim 1, wherein the wavenumber is estimated by directly relating a spatial derivative of phase to the wavenumber as defined over a two-dimensional wave field using the proportionality of the spatial derivative in two dimensions of phase to the wavenumber.

\* \* \* \* \*